US008218291B2

(12) United States Patent
Silvi et al.

(10) Patent No.: US 8,218,291 B2
(45) Date of Patent: Jul. 10, 2012

(54) MONOMERS FOR PREPARING POLYCARBONATE RESINS, METHODS OF PREPARING THE MONOMERS, POLYCARBONATE RESINS PREPARED WITH THE MONOMERS, AND CAPACITORS COMPRISING THE POLYCARBONATE RESINS

(75) Inventors: Norberto Silvi, Clifton Park, NY (US); Gary Charles Davis, Albany, NY (US); Patrick Joseph McCloskey, Watervliet, NY (US); Sheldon Jay Shafer, Clifton Park, NY (US); Julia Lam Lee, Niskayuna, NY (US); Yang Cao, Niskayuna, NY (US); Patricia Chapman Irwin, Altamont, NY (US)

(73) Assignee: General Electric Company, Niskayuna, NY (US)

( * ) Notice: Subject to any disclaimer, the term of this patent is extended or adjusted under 35 U.S.C. 154(b) by 293 days.

(21) Appl. No.: 12/751,649

(22) Filed: Mar. 31, 2010

(65) Prior Publication Data

US 2011/0242729 A1    Oct. 6, 2011

(51) Int. Cl.
    *H01G 9/00*    (2006.01)
(52) U.S. Cl. ........ 361/523; 361/516; 361/519; 361/525; 361/528; 361/529; 29/25.01; 29/25.03

(58) Field of Classification Search ............ 361/523, 361/516, 517, 519, 525, 528–529, 531, 534; 29/25.01, 25.03
    See application file for complete search history.

(56) References Cited

U.S. PATENT DOCUMENTS

| | | | | |
|---|---|---|---|---|
| 4,880,874 | A * | 11/1989 | Hirai et al. | 525/67 |
| 5,447,989 | A * | 9/1995 | Mylonakis et al. | 525/67 |
| 5,800,955 | A * | 9/1998 | Kashimura et al. | 430/59.6 |
| 6,151,042 | A * | 11/2000 | Smith et al. | 347/20 |
| 6,437,029 | B1 * | 8/2002 | Lim et al. | 524/97 |
| 7,186,767 | B2 * | 3/2007 | Seidel et al. | 524/127 |
| 7,446,234 | B2 * | 11/2008 | More et al. | 568/718 |
| 7,495,064 | B2 | 2/2009 | Domingo et al. | |
| 2009/0186967 | A1 | 7/2009 | Akada et al. | |

* cited by examiner

*Primary Examiner* — Nguyen T Ha
(74) *Attorney, Agent, or Firm* — Mary Louise Gioeni

(57) ABSTRACT

A monomer and polycarbonate resin are provided, as are methods of making the monomer. The resin may be used to provide a thin film that has a higher dielectric constant and higher glass transition temperature, and similar breakdown strength and similar dissipation factor to films prepared from polycarbonate resins not so modified. The thin films, in turn, may advantageously be used to form, wholly or in part, articles such as capacitors, sensors, batteries, flexible printed circuit boards, keyboard membranes, motor/transformer insulations, cable wrappings, industrial tapes, interior coverage materials, and the like. In particular, a capacitor comprising the polycarbonate resin is also provided.

19 Claims, 9 Drawing Sheets

MONOMERS FOR PREPARING POLYCARBONATE RESINS, METHODS OF PREPARING THE MONOMERS, POLYCARBONATE RESINS PREPARED WITH THE MONOMERS, AND CAPACITORS COMPRISING THE POLYCARBONATE RESINS

BACKGROUND

This invention generally relates to monomers and methods for preparing them. Polycarbonate resins prepared with the monomers and capacitors comprising the polycarbonate resins are also provided.

Because of their transparency, toughness and relatively low cost, polycarbonates are useful in a wide variety of applications and are produced globally on a scale of well over a billion pounds annually. But one example of an industrially important use of polycarbonate is in the manufacture of capacitors.

Over the last decade, significant increases in capacitor reliability have been achieved through a combination of advanced manufacturing techniques and new materials. Greatly enhanced performance has been obtained particularly in so-called film capacitors. Film capacitors can be classified into three types based on the manufacturing technology, namely, film and foil capacitors, metallized film capacitors and mixed technology film capacitors.

Generally, metallized film capacitors consist of two metal electrodes separated by a layer of plastic film. The metallized plastic film is constructed by vacuum depositing metal film onto a layer of plastic film. This would offer compact capacitor structure, self-clearing capability, longer lifetime, and higher energy density. Some of the commonly used plastic films are polypropylene and polyester films. The metal film layer is typically extremely thin, in the order of about 50-500 angstroms and is typically aluminum or zinc or alloys of such. Compared to other types of capacitors, metallized film capacitors have advantage in size, simplicity, and cost of manufacturing, and hence been widely used in the power electronics industry.

While significant improvements have been made in metallized film capacitors, certain issues, such as thermal stability and reduced lifetime continue to present challenges to their widespread adoption. For example, polycarbonates made from phosgene and BPA have been used in the past for the manufacture of thin film capacitors, as have polypropylene and certain polyesters. However, the glass transition temperature of these materials (generally speaking, 150° C. or lower) limits the continuous-use, working temperatures of articles made from these resins to only about 120° C. or less. Furthermore, the low dielectric constant (about 2.9 @ 1 MHz, for polycarbonate resins) of these resins limits the stored energy of capacitors made from these materials to about 1 Joule/cc.

New polymeric resins would thus desirably be provided, having higher dielectric constants, and capable of operating at operating temperatures in excess of 120° C. Such resins would be expected to be useful in a wide variety of articles, including thin film capacitors, and metalized thin film capacitors in particular.

BRIEF DESCRIPTION OF THE INVENTION

There is provided a polycarbonate resin, having a repeating unit of the formula I:

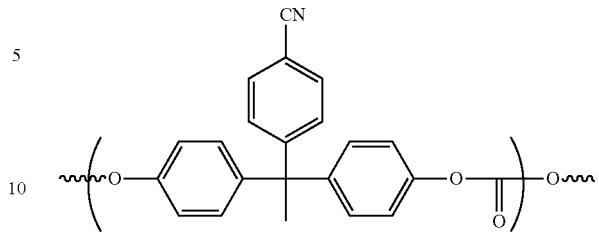

A capacitor is also provided comprising a thin film of a polycarbonate resin having a repeating unit of formula I:

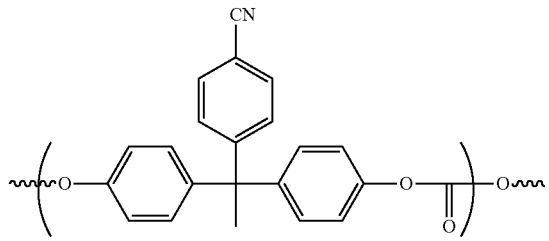

The capacitor also includes a metalized layer disposed on a first surface of the polycarbonate film, and an electrode disposed on a second surface of the polycarbonate film.

A monomer is also provided having a formula IV:

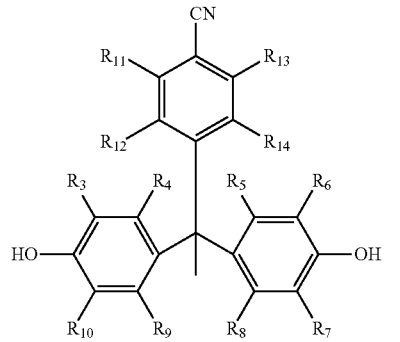

Wherein $R_3$-$R_{10}$ are independently a hydrogen atom, halogen atom, nitro group, cyano group, $C_1$-$C_{20}$ alkyl radical $C_4$-$C_{20}$ cycloalkyl radical, or $C_4$-$C_{20}$ aryl radical; $R_{11}$-$R_{14}$ are each independently a hydrogen atom, $C_1$-$C_{20}$ alkyl radical, $C_4$-$C_{20}$ cycloalkyl radical, or $C_4$-$C_{20}$ aryl radical; or $R_{11}$ and $R_{12}$ together form a $C_4$-$C_{20}$ cycloaliphatic ring which is optionally substituted by one or more $C_1$-$C_{20}$ alkyl, $C_6$-$C_{20}$ aryl, $C_5$.$C_{20}$, aralkyl, $C_5$-$C_{20}$cycloalkyl groups or a combination thereof.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
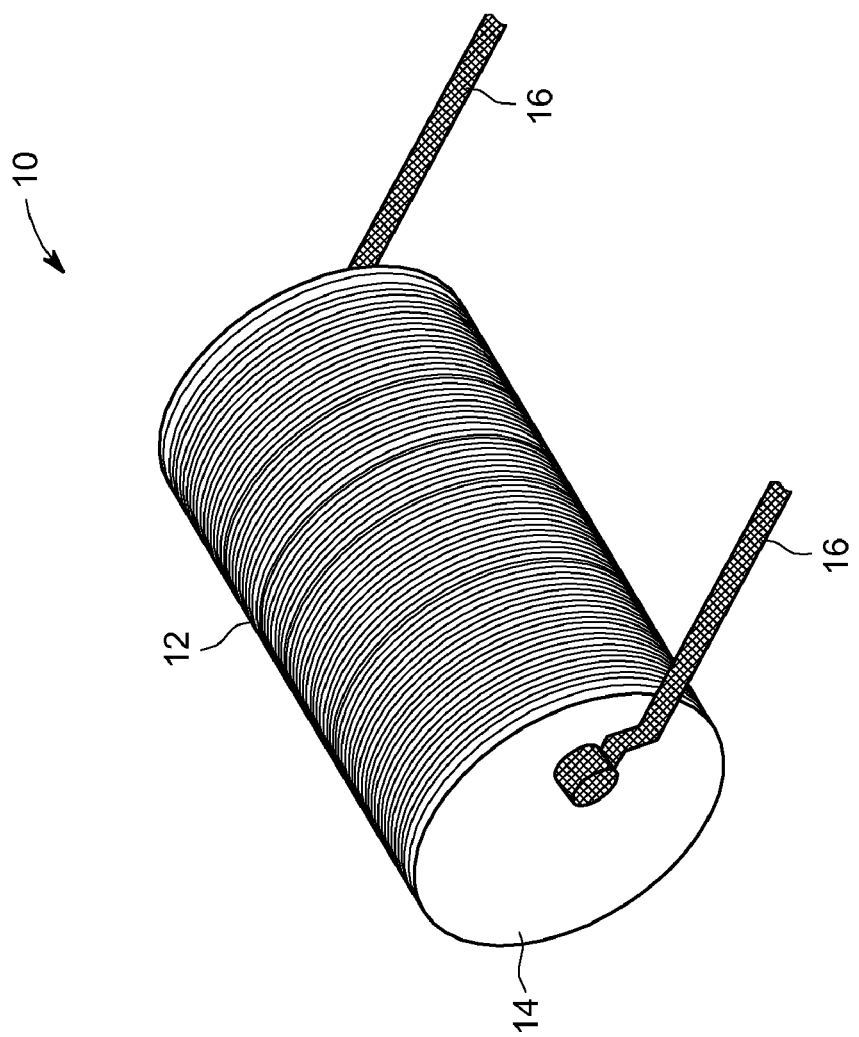
FIG. 1 is a diagrammatic illustration of an exemplary metallized film capacitor in accordance with aspects of the invention.

The compositional ranges disclosed herein are inclusive and combinable (e.g., ranges of "up to about 25 wt %", or, more specifically, "about 5 wt % to about 20 wt %", are inclusive of the endpoints and all intermediate values of the ranges). Weight levels are provided on the basis of the weight of the entire composition, unless otherwise specified; and ratios are also provided on a weight basis. Moreover, the term "combination" is inclusive of blends, mixtures, alloys, reaction products, and the like. Furthermore, the terms "first," "second," and the like, herein do not denote any order, quantity, or importance, but rather are used to distinguish one element from another. The terms "a" and "an" herein do not denote a limitation of quantity, but rather denote the presence of at least one of the referenced items. The modifier "about" used in connection with a quantity is inclusive of the stated value, and has the meaning dictated by context, (e.g., includes the degree of error associated with measurement of the particular quantity). The suffix "(s)" as used herein is intended to include both the singular and the plural of the term that it modifies, thereby including one or more of that term (e.g., "the refractory element(s)" may include one or more refractory elements). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

Two of the dielectric properties considered herein are dielectric constant and breakdown strength. The "dielectric constant" of a dielectric is a ratio of capacitance of a capacitor, in which the space between and around the electrodes is filled with the dielectric, to the capacitance of the same configuration of electrodes in a vacuum. As used herein, "breakdown strength" refers to a measure of dielectric breakdown resistance of a dielectric material under an applied AC or DC voltage. The applied voltage prior to breakdown is divided by thickness of the dielectric material to give the breakdown strength. It is generally measured in units of potential difference over units of length, such as kilovolts per millimeter (kV/mm), or volts per micron (V/micron). The "dissipation factor (Df)" of a dielectric is a measure of the electric loss in a dissipative system. If a capacitor is used in an AC circuit, the dissipation factor due to the non-ideal capacitor is expressed as "tan delta", which is the ratio of the resistive power loss in the equivalent series resistance (ESR) to the reactive power oscillating in the capacitor.

The polycarbonate resins described herein, having a repeating unit of formula I:

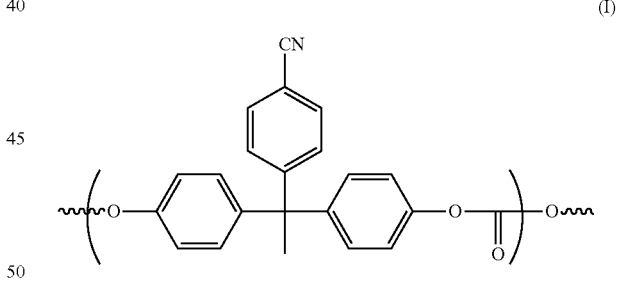

(I)

And a formula according to Formula H

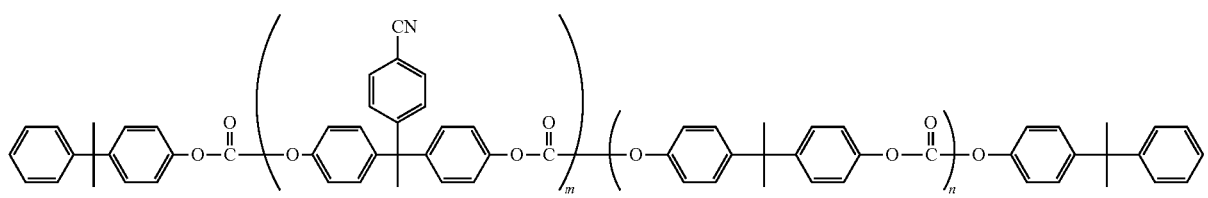

(II)

exhibit a glass transition temperature and dielectric constant that renders them suitable for use in the fabrication of electronic articles, such as, e.g., thin film capacitors, including metallized thin film capacitors. The resins are prepared from a carbonate source and a mixture of at least two sources of hydroxyl groups, at least one of which comprises the inventive monomer. The use of a mixture of hydroxyl group sources, including the inventive monomer, has now surprisingly been discovered to increase the glass transition temperature of the resulting polycarbonates to as high as 150° C., 170° C., 190° C., 210° C., or higher. The dielectric constant is also surprisingly increased in thin films prepared from the polycarbonates, e.g., to as at least about 2.5, or about 2.75, or about 3.0, or about 3.25, or about 3.5, or about 3.75, or about 4.0, or even about 4.25, or even as high as 4.3. These increases are further provided without appreciably affecting the dielectric loss or breakdown strength of the polycarbonate resins.

The polycarbonate resins provided herein can be prepared from a carbonate source and a mixture of at least two sources of hydroxyl groups. The carbonate source may be one or more of phosgene, diphosgene, triphosgene, a halogen formate and/or a carboxylate acid diester. In some embodiments, the carbonate source comprises phosgene. The hydroxyl source(s) may include a combination of at least two bisphenols, one of which desirably comprising the monomer provided herein.

One of the bisphenols desirably has a formula according to Formula III:

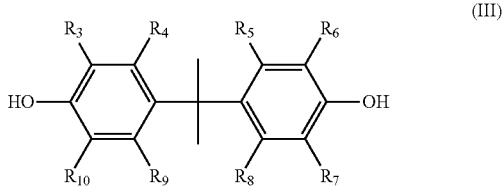

(III)

wherein $R_3$-$R_{10}$ are independently a hydrogen atom, halogen atom, nitro group, cyano group, $C_1$-$C_{20}$ alkyl radical $C_4$-$C_{20}$ cycloalkyl radical, or $C_6$-$C_{20}$ aryl radical.

Suitable bisphenols according to Formula III are exemplified by, but not limited to, 2,2-bis(4-hydroxyphenyl)propane (bisphenol A); 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene and 1,4-bis(2-(4-hydroxy-3-methylphenyl)-2- propyl)benzene. In some embodiments, the at least one bisphenol according to Formula III may desirably be bisphenol A.

The combination of hydroxyl sources also desirably includes the inventive monomer according to Formula IV:

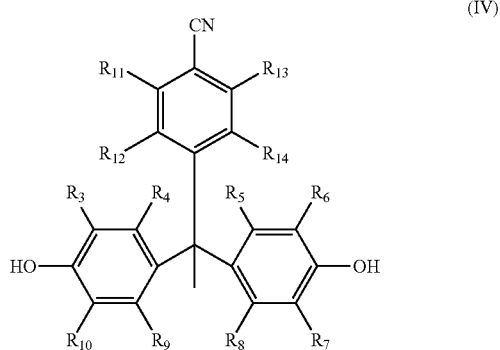

Wherein $R_3$-$R_{10}$ are independently a hydrogen atom, halogen atom, nitro group, cyano group, $C_1$-$C_{20}$ alkyl radical $C_4$-$C_{20}$ cycloalkyl radical, or $C_4$-$C_{20}$ aryl radical; $R_{11}$-$R_{14}$ are each independently a hydrogen atom, $C_1$-$C_{20}$ alkyl radical, $C_4$-$C_{20}$ cycloalkyl radical, or $C_4$-$C_{20}$ aryl radical; or $R_{11}$ and $R_{12}$ together form a $C_4$-$C_{20}$ cycloaliphatic ring which is optionally substituted by one or more $C_1$-$C_{20}$ alkyl, $C_6$-$C_{20}$ aryl, $C_5$.$C_{20}$, aralkyl, $C_5$-$C_{20}$cycloalkyl groups or a combination thereof. In some embodiments, the inventive monomer according to formula IV may desirably be cyano-bisphenol A. Although the cyano group is shown at position 1 in the above formula IV, it is to be understood that the cyano group may be at any position on the ring on which it is shown, in which case $R_{11}$-$R_{14}$ will be adjusted accordingly.

Suitable inventive monomers according to Formula IV may be prepared by the method also provided herein. More specifically, inventive monomers according to Formula IV can be prepared from acid catalyzed reaction of phenol with 4-acetoxy benzonitrile, ketones and some aldehydes. In some embodiments, the inventive monomer according to Formula IV is prepared from the acid catalyzed reaction of phenol with 4-acetoxy benzonitrile.

The acid catalyzed reaction can be performed with soluble mineral acids and/or soluble organic acids. Suitable examples of soluble mineral acids include, but are not limited to, hydrobromic, hydrofluoric, phosphoric, sulfuric and hydrochloric acids. In some embodiments, the soluble mineral acids may be sulfuric acid or hydrochloric acid and in others, the soluble mineral acid may be hydrochloric acid. Suitable examples of soluble organic acids include, but are not limited to, methane sulfonic acid, trifluoro methane sulfonic acid, toluene sulfonic acid, benzene sulfonic acid, and the like. In some embodiments, the soluble organic acid may be methane sulfonic acid.

Alternatively, the preparation method can employ heterogeneous catalysis with sulfonic acid ion exchange resin beads. The concept of heterogeneous catalysis in ion exchange resin beads is disclosed, e.g., in U.S. Pat. No. 2,366,007. In such embodiments, the resin may be modified by ionically attaching a mercaptan promoter, to provide an attached promoter resin. Suitable mercaptan promoters are disclosed, for example, in U.S. Pat. No. 2,359,242, while attached promoters are generally discussed in U.S. Pat. No. 3,394,089. The reaction can also be performed with a bulk promoter system, where the promoter is not attached to the resin, but is soluble in the reaction matrix.

In some embodiments, the molar ratio of the bisphenol according to Formula III to the inventive monomer according to formula IV (herein after the ratio of Formula III/Formula IV) may be adjusted to provide polycarbonate resins having different properties. For example, the ratio of Formula III/Formula IV may generally be from about 99:1 to about 0:100. Lower ratios of Formula III/Formula IV, e.g., 0:100, would generally be expected to result in polycarbonates having higher glass transition temperatures and higher dielectric constants, while higher ratios of Formula III/Formula IV, e.g., 99:1 would be expected to result in polycarbonates having lower glass transition temperatures and lower dielectric constants.

There seems to be a ratio of Formula III/Formula IV for which the dielectric constant of the polymer reaches a maximum value, and for values of Formula III/Formula IV different than this ratio the dielectric constant of the resulting polymer is lower than that obtained for this ratio. The polycarbonate resin for which the dielectric constant reaches its maximum value seems to contain between 20 and 30 mole % of the Formula IV monomer. And so, for embodiments of the invention wherein the dielectric constant is desirably maximized, the ratio of Formula III/Formula IV can be between 4/1 or between about 2.3/1.

Figure 10:
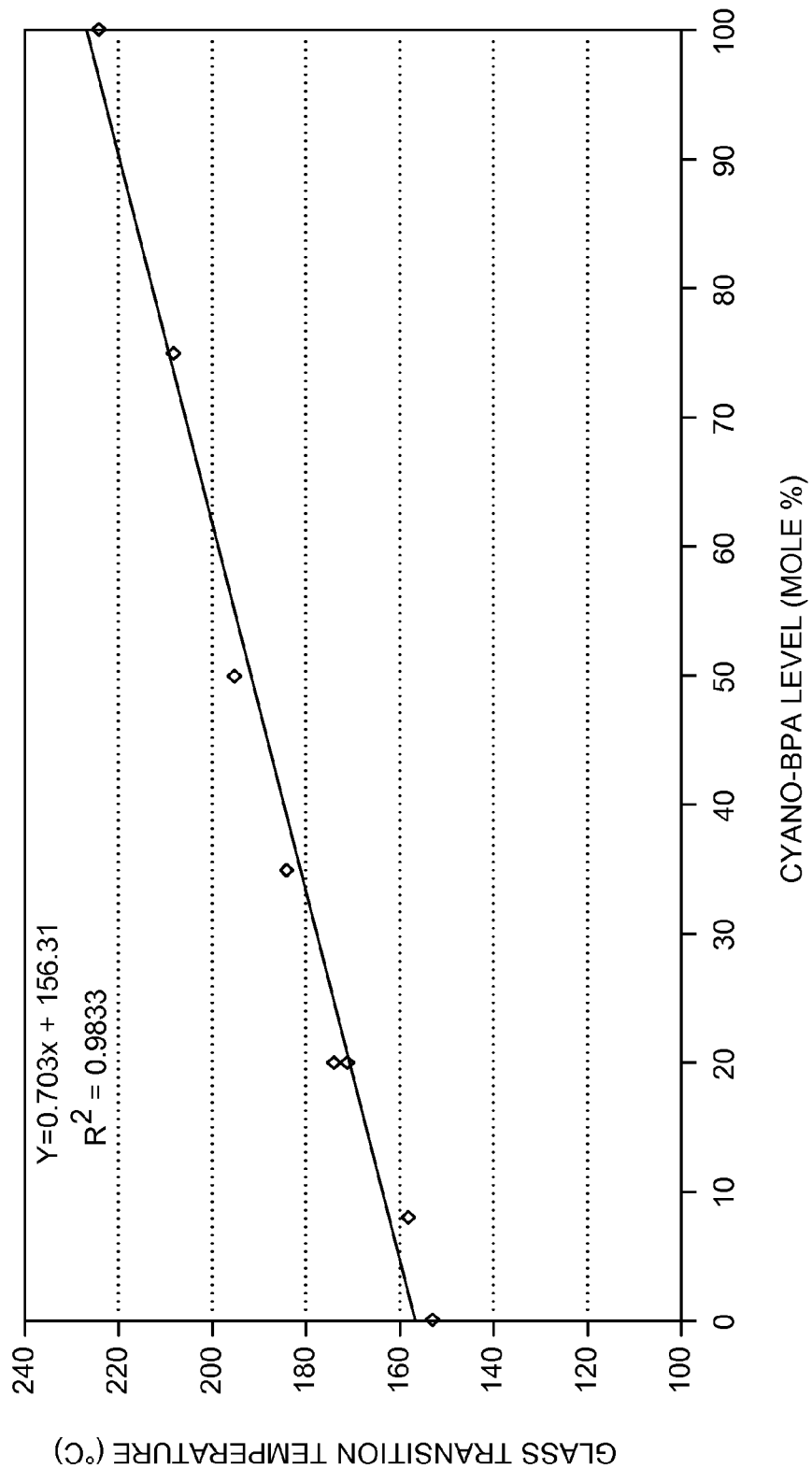
FIG. 10 is a graphical depiction of the effect of inventive monomer level on the Tg of a polycarbonate resin according to one embodiment.

As shown in FIG. 10, the glass transition temperature of the polymer containing different levels of Formula III and Formula IV, on the other hand, increases monotonically with the amount of Formula IV added to the formulation according to the formula Tg (° C.)=0.7*Formula IV level (in mole %)+156.3. Therefore, for example, a polymer containing 20 mole % of the inventive monomer according to Formula IV would have a glass transition temperature of approximately 170° C.

The polycarbonate resins may advantageously be prepared utilizing interfacial polymerization. Typically, interfacial polymerization involves a reaction mixture comprising the above-described carbamate and hydroxyl sources, water, at least one water immiscible solvent, an acid acceptor, and a catalyst.

The interfacial polymerization may be carried out in any water immiscible solvent. Suitable water immiscible solvents include, but are not limited to chlorinated aliphatic hydrocarbons, such as methylene chloride, carbon tetrachloride, dichloroethane, trichloroethane and tetrachloroethane, substituted aromatic hydrocarbons such as chlorobenzene, o-dichlorobenzene and the various chlorotoluenes. In some embodiments, the chlorinated aliphatic hydrocarbons, especially methylene chloride, are suitable for use as the water immiscible solvent.

The polymerization is also desirably carried out in the presence of at least one acid acceptor. Suitable acid acceptors include, for example, alkali metal or alkaline earth metal hydroxides. In some embodiments, lithium hydroxide, sodium hydroxide, potassium hydroxide and calcium hydroxide may be used. In some embodiments, sodium and/or potassium hydroxides are desirably used as the acid acceptor. Combinations of acid acceptors may also be utilized.

Any catalyst, or combination of catalyst(s), suitable for use in interfacial conditions may be utilized. As such, the catalyst may comprise one or more tertiary amines. Suitable tertiary amines are exemplified by triethylamine, tributyl amine, trioctyl amine, N-ethylpiperidine, N-butyl-N,N-dimethylamine, Hönig's Base, N-methylpiperidine, 4-(N,N-dimethylamine)

pyridine, N-ethylemorpholine, N-propylpiperidine, 1,4-diazabicyclo[2.2.2]octane, 1,5-diazabicyclo[4.3.0]non-5-ene, and the like.

In some embodiments, the catalyst may comprise a quaternary ammonium compound such as tetrabutylammonium/tributylbenzylammonium/tetramethylammonium hydroxide/chloride/bromide/hydrogen sulfate/tetrafluoroborate. Specific examples of suitable quaternary ammonium compounds include, but are not limited to, tetramethylammonium hydroxide, tetrabutylammonium hydroxide, and the like.

In alternate embodiments, the catalyst(s) may comprise the phosphonium compounds corresponding to the quaternary ammonium compounds, e.g., tetrabutylphosphonium/tributylbenzylphosphonium/tetramethylphosphonium hydroxide/chloride/bromide/hydrogen sulfate/tetrafluoroborate. Exemplary quaternary phosphonium salts include, but are not limited to, tetrabutylphosphonium hydroxide, tetraoctyphosphonium hydroxide, tetrabutylphosphonium acetate, and the like.

The desired catalyst, or combination of catalysts, may be utilized in any effective amount, as is readily determined by those of ordinary skill in the art. Generally speaking, the total amount of catalyst(s) may be between about 0.001 mol % to about 10 mol % based upon the total moles of bisphenols employed. In some embodiments, from about 0.01 mol % to about 8 mol %, or from about 0.05 mol % to about 5 mol %, total catalyst may be used based upon total moles of bisphenols utilized.

Any of the conventional additives for polycarbonates may also be added to the polycarbonates, and may be added in conventional amounts. Additives such as stabilizers, mold release agents, flow auxiliaries, antistatic agents, impact modifiers, flame retardants, colorants, fillers, may be added as desired in consideration of the end use of the polycarbonate. Suitable examples of such additives are described, e.g., in "Additives for Plastics Handbook", John Murphy, Elsevier, Oxford, 1999.

Particular examples of stabilizers include organic phosphites, phosphonates and phosphanes, and substituted benzotriazoles. Mold release agents may typically be exemplified by derivatives of long chain fatty acids such as pentaerythritol tetrastearate and glycerol monostearate. If used, stabilizers and/or mold release agents may typically be employed in amounts of from about 0.02 wt % to about 1 wt % based upon the total weight of the polycarbonate.

If flame retardants are desirably included in the polycarbonate, phosphate esters, such as triphenyl phosphate, resorcinol diphosphoric acid esters, bromine-containing compounds, such as brominated phosphoric acid esters, brominated oligocarbonates and polycarbonates, or salts of fluorinated organic sulfonic acids may be used.

Suitable impact modifiers include graft polymers comprising one or more graft bases chosen from at least one polybutadiene rubber, acrylate rubber, ethylene/propylene rubbers, and grafting monomers chosen from the group consisting of styrene, acrylonitrile or alkyl methacrylate, or interpenetrating siloxane and acrylate networks with grafter-on methyl methacrylate or styrene/acrylonitrile.

Furthermore, colorants, such as organic dyestuffs or pigments or IR absorbers, may be added, individually, or in combination with stabilizers.

Any such additives can be added to the polymer melt individually or in any desired mixtures, or number of mixtures, or on isolation of the polymer or after melting polymer granules in a compounding step. Further, the additives or mixtures thereof may be added to the polymer melt as a solid, i.e., as one or more powders, or as a melt. Or, any desired additives may be incorporated into the polycarbonate by use of a master batch or mixtures of master batches of the additives or additive mixtures.

The polycarbonate resins may also comprise one or more fillers, such as organic or inorganic fillers of any shape and dimension. In some embodiments, the polycarbonate resins may be filled with functionalized or unfunctionalized fillers of nanometer dimensions, e.g., from about 0.1 nm to about 1000 nm, to improve the properties of these resins even further. Polymers containing certain nanoparticles or nanofillers such as barium titanate, aluminum oxide ($Al_2O_3$) or silica have been found to show higher corona resistance and dielectric constant, and may be particularly well suited to the inventive films and capacitors. Particle filled polymers also could offer increased thermal conductivity and may be suitable for use in the invention. Films made from composite resins according to such embodiments may contain a relatively small amount (less than about 10 to 20 weight percent or so based upon the total weight of the resin) of the filler, which will desirably be uniformly dispersed into the polymer.

Any desired filler(s) can be added to the resin while the resin is being made (in-situ polymerization) or in a subsequent step by using some type of mixing equipment, such as extruders. The extruders used to disperse the filler into the polymer, and to generate the melt to produce extrusion cast films can be of the single- or twin-screw type. However prepared, in those embodiments where fillers are desirably utilized, the method utilized to add the filler will desirably facilitate the relatively uniform distribution of the filler throughout the resin, which is expected to assist in the provision of the desired properties in the resulting resin.

In some embodiments, it may be desirable to include a chain stopper in the reaction mixture. Monofunctional phenols, such as phenol, 4-phenylphenol, cardanol, eugenol, 4-t-butylphenol, p-cumylphenol, 3,5-dimethylphenol and 2,4-dimethylphenol. The amount of chainstopper used may be from about 0.1 mol % and 7 mol % based on the total number of moles of bisphenol(s) used.

The polycarbonates may be prepared by reacting the mixture of the bisphenol according to formula III and the inventive monomer according to formula IV with an excess of the carboxyl source, e.g., phosgene, under interfacial reaction conditions in which the pH is from about 9.5 to about 12. As used herein, excess phosgene means an amount of phosgene which represents between about 3 and about 200 mole percent excess phosgene relative to the number of moles of bisphenol employed.

The interfacial reaction may be carried out in any suitable reaction vessel, such as a stirred tank reactor, or in any combination of reaction vessels in a batch or semi-batch process. In some embodiments, the reaction may be carried out in one or more continuous flow reactors. The type of flow reactor is not particularly limited, and may be any reactor system which provides for the upstream introduction of the reaction mixture, water, water immiscible solvent, acid acceptor and catalyst, and the downstream removal of polycarbonate. In some embodiments, the flow reactor may comprise a series of tubular reactors. In other embodiments, the flow reactor may comprise a series of continuous stirred tank reactors.

The polycarbonate resins provided can have a weight average molecular weight (Mw) of from about 10,000 to about 200,000, or from about 15,000 to about 100,000, or from about 20,000 to about 80,000. Although the resins are suitable for use in a wide variety of applications, the relatively high molecular weight of these resins make them good candidates for the fabrication of thin films, e.g., of 50 microns in thickness and less, 30 microns in thickness or less, or even 10 microns in thickness or less, either from a melt (compression molding, extrusion cast) or from solution (solvent cast, spin cast).

In such embodiments, the resulting films, which may be either uniaxially or biaxially oriented, are expected to exhibit improved mechanical and dielectric properties as compared with films made from other polymers and even other polycarbonates made using only a single bisphenol, e.g., bisphenol A. For example, thin films prepared from the polycarbonate resins are expected to exhibit dielectric constants 2.5, or about 2.75, or about 3.0, or about 3.25, or about 3.5, or about 3.75, or about 4.0, or even about 4.25, or even as high as 4.3. Further, the room temperature breakdown strength of these films can be as high as 550 V/micron, as measured in solvent-cast films of approximately 15 microns in thickness. As mentioned above, composite or unfilled films may be prepared, and the use of fillers, e.g., of nanometer dimensions of from about 0.1 nm to about 1000 nm, in amounts of less than about 20 wt %, or less than about 10 wt %, based upon the total weight of the film, is expected to further enhance the dielectric properties of the film, such as dielectric constant and voltage endurance, among others. The films can also be metallized, if desired.

Electronic articles may thus advantageously be prepared, partly or entirely, from such thin films. Examples of electronic articles that may benefit from the enhanced properties of the thin films include capacitors, sensors, batteries, flexible printed circuit boards, keyboard membranes, motor/transformer insulations, cable wrappings, industrial tapes, or interior coverage materials.

In some embodiments, the thin films may be used, e.g., as the dielectric layer of metallized film electrostatic capacitors. A typical metallized film capacitor includes a polymer film interposed between two electrodes on either side. The two electrodes include a layer of a metal such as aluminum, copper or zinc or their combination that is vacuum deposited on the polymer film that acts as a dielectric in the metallized film capacitor. In one embodiment of the present invention, a metallized film capacitor disclosed herein includes an electrode, typically made of a metal layer such as aluminum or zinc disposed (e.g., vacuum deposited) upon a first surface of a dielectric layer comprising the polycarbonate resin.

Turning now to the drawings, FIG. 1 is a diagrammatic illustration of a metallized film capacitor 10 in accordance with aspects of the invention. The metallized film capacitor 10 includes plastic foils 12 wound around a cylindrical surface 14 of the capacitor as final packaging. Lead wires 16 provide electrical connection for the metallized film capacitor 10 in a circuit. Technology used in the exemplary embodiment in constructing the metallized film capacitor is referred to as "wound" capacitor technology. In the "wound" capacitor technology, offset lengths of metallized foils are wound in a rolled cylinder. Metallized film capacitors in accordance with the invention are expected to provide electrical characteristics such as low dielectric loss factor and could be widely used for power electronics applications.

Figure 2:
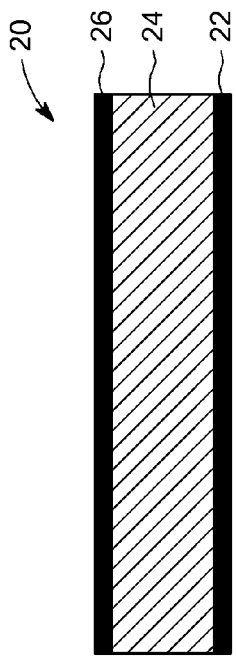
FIG. 2 is a cross-sectional view of a portion of a metallized film capacitor, illustrating a dielectric layer comprising a polycarbonate resin in accordance with one aspect of the invention.

FIG. 2 represents a cross-sectional view of a portion of a metallized film capacitor 20 in accordance with the invention. The metallized film capacitor 20 includes an electrode 22, for example a cathode, upon which a dielectric layer 24 is disposed. In one example, the dielectric layer 24 is a thin film comprising the polycarbonate resin. Further, a metallized layer 26 is disposed on the dielectric layer 24, and acts as an anode.

The electrode 22 typically includes metal foils. In one embodiment, the electrode 22 includes at least one of aluminum, copper, or zinc foil. Thickness of the dielectric layer 24 may be less than about 50 microns. In another exemplary embodiment, the thickness of the dielectric layer 24 may be less than 30 microns, or even less than 10 microns. Breakdown voltage of the dielectric layer 24 may be at least about 275 kV/mm. The typical thickness of the metallized layer 26 may be in the range of from about 50 Å to about 500 Å.

Figure 3:
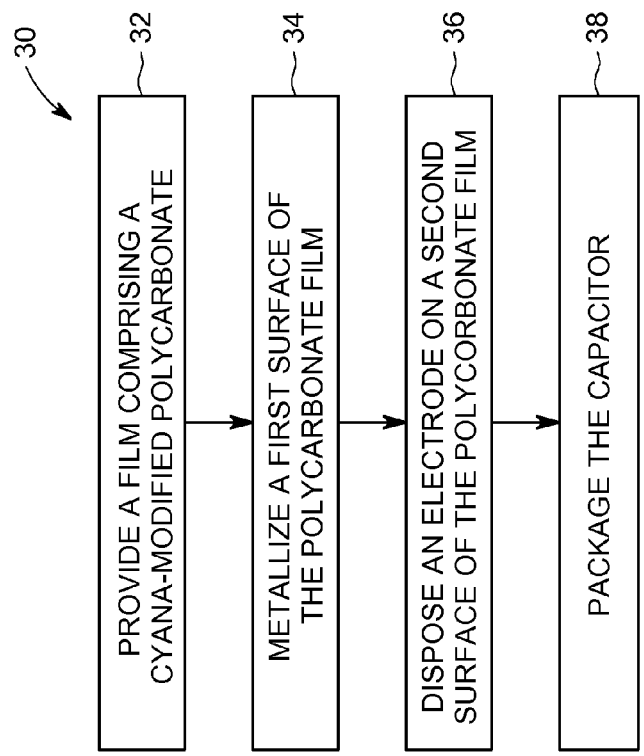
FIG. 3 is a flow chart representing steps in an exemplary method of making a metallized film capacitor with a dielectric layer comprising a polycarbonate resin as in FIG. 2, in accordance with one aspect of the invention.

FIG. 3 is a flow chart illustrating exemplary steps involved in a method 30 of making a metallized film capacitor 20 as referenced to in FIG. 2, according to an aspect of the invention. The method 30 includes providing a film comprising a cyano-modified polycarbonate at step 32.

A first surface of the polycarbonate film is then metallized at step 34. The metallizing at step 34 may include process of vapor deposition, sputtering or electrochemical deposition of the polycarbonate film. In an example, the process of vapor deposition, sputtering or electrochemical deposition may include depositing aluminum or copper, alone or in combination with zinc, on a first surface of the polycarbonate film. The method 30 also includes disposing an electrode on a second surface of the polycarbonate film at step 36. Finally, the metallized film capacitor is packaged at step 38. The step 38 of packaging the capacitor will typically include winding and laminating the capacitor, and providing conductors or terminals for applying charge to the wound layers.

Figure 4:
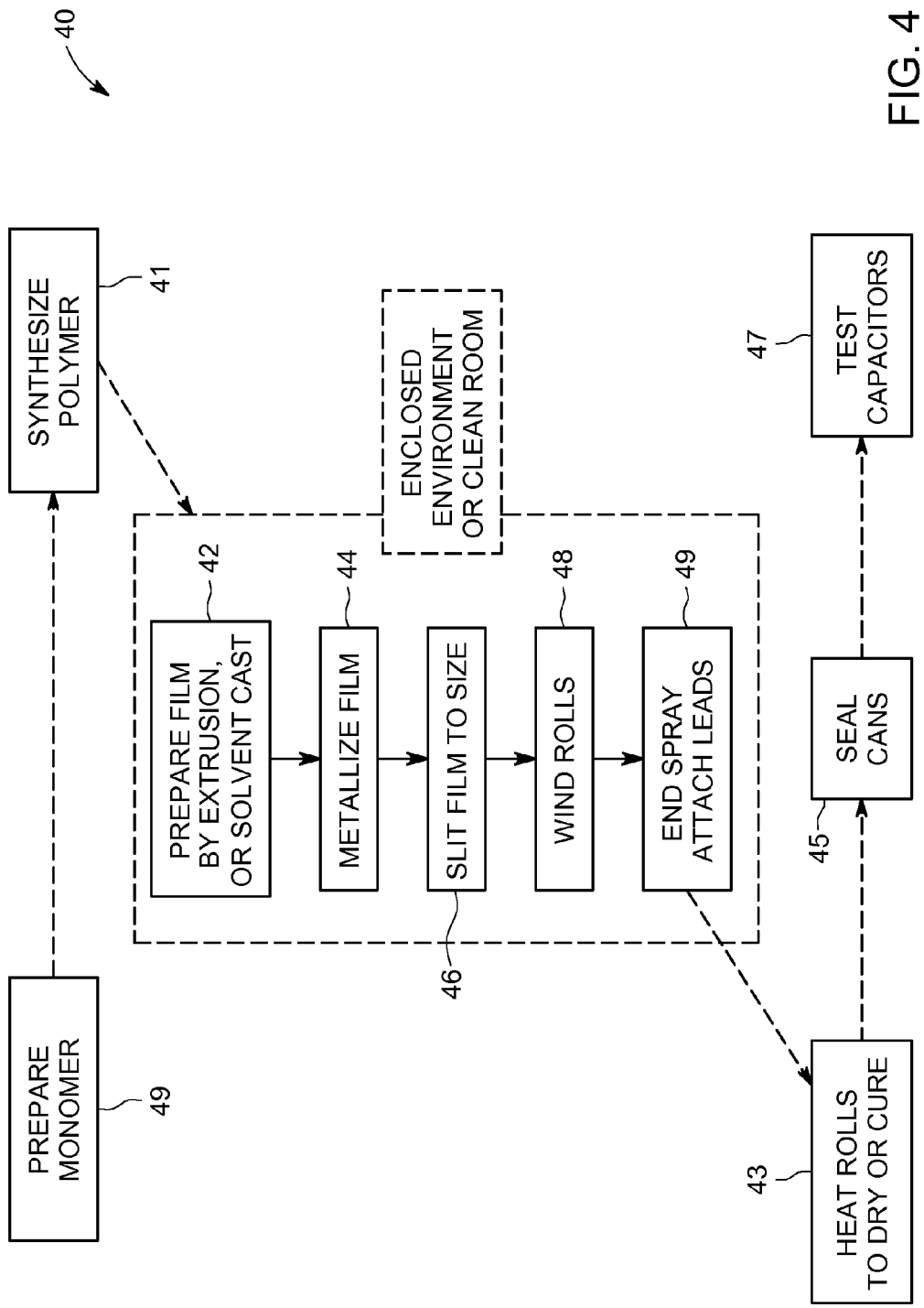
FIG. 4 is a flow chart representing steps in an exemplary method of making a metallized film capacitor with a dielectric layer comprising a polycarbonate resin as in FIG. 2, in accordance with one aspect of the invention.

FIG. 4 is a flow chart illustrating exemplary steps involved in a method 40 of making a metallized film capacitor 20 as referenced to in FIG. 2, according to an aspect of the invention. The method 40 includes preparing a film comprising a cyano-modified polycarbonate at step 42. Method 40 also shows the optional preliminary steps of synthesizing the monomer and also the polymer at step 41, and described in detail above.

A first surface of the polycarbonate film is then metallized at step 44. The metallizing at step 44 may include process of vapor deposition, sputtering or electrochemical deposition of the polycarbonate film. The method 40 also includes slitting the metalized film to the desired size at step 46. The metallized film capacitor is then wound at step 48. The ends of the capacitor are sprayed with zinc alloys and leads attached at step 49. Desirably, steps 42, 44, 46, 48 and 49 are carried out in a clean room environment.

Method 40 may further include the optional steps of heating the capacitors (43), sealing the cans (45), and testing the capacitors (47). If desired, heating the capacitors may involve heating in a vacuum oven at a time and temperature appropriate for the capacitor, and within the level of ordinary skill in the art. The cans may optionally be sealed at step 45 using conventional injection molding procedures with polyester or epoxy resins. At step 47 the capacitors may be tested, e.g., as by capacitance retention and dissipation factor at different temperatures and frequencies, breakdown voltage, insulation resistance, and the like.

Since the energy stored by a capacitor per unit volume of the capacitor increases with the dielectric constant of the dielectric medium, a higher dielectric constant of the insulating layer of the capacitor would result in a higher stored energy density, or stored energy per unit volume of the capacitor. A higher breakdown strength of the dielectric layer (in V/micron) would also result in a higher energy density of the capacitor. Such capacitors would also be expected to have a higher voltage rating and/or higher resistance to corona discharge compared to capacitors made from other polymer films.

EXAMPLES

The examples presented below are intended to be merely illustrative, and should not be construed to be any sort of limitation on the scope of the claimed invention.

Example 1

Preparation of the Inventive Monomer According to Formula IV by Soluble Mineral Acid Method To a 1 liter 3-neck flask was added 517.7 grams (5.51 moles) of phenol and 9.52 grams (0.053 moles) 3-Mercapto propane sulfonic acid sodium salt. The mixture was heated to 55° C. to melt the phenol and to this stirred mixture was added drop wise 28.43 grams (0.29 moles) of sulfuric acid. To this stirred mixture was added 100.06 grams (0.689 moles) of 4-acetoxy benzonitrile. The reaction mixture was stirred at 55° C. and periodic samples were removed for analysis of the reaction mixture by HPLC. The ratio of unreacted 4-acetoxy benzonitrile versus the product bisphenol was monitored. The reaction was maintained for ~21 hours at which time the rate of formation of the bisphenol had slowed dramatically. To the mixture was added 1 gram of 3-mercapto propane sulfonic acid sodium salt and 3 grams of sulfuric acid. The reaction was continued for an additional 4 hours without any change in the bisphenol production. The reaction was terminated. The warm reaction mixture was transferred to a 4 Liter beaker where it was stirred with 3 Liters of dichloromethane. The resulting solid was filtered from the solution. The crude solid was re-crystallized twice from hot methanol/water mixture. The resulting crude solid was slurried with chloroform to remove some un-reacted 4-acetoxy benzonitrile. The solid was then re-crystallized twice more from hot methanol/water mixture. The resulting white solid was vacuum dried overnight at 80° C. and 29" of vacuum. The dried solid had a weight of 137.2 grams (63%) a HPLC purity of 99% and a melting point of 212.5° C.-214° C.

Example 2

Preparation of the Inventive Monomer According to Formula IV by Insoluble Ion Exchange Resin with Attached Promoter a. Preparation of the Attached Promoter Resin A one-pound sample of Rohm&Haas Amberlyst A-121 resin was washed with de-ionized water than vacuum dried at 100° C. overnight at 29" of vacuum. To a 3 Liter 3-neck flask equipped with paddle agitator and gas sparge tube was added 920 ml of 18-Mega ohm de-ionized water. The solution was stirred and nitrogen was sparged through the de-ionized water to remove traces of dissolved oxygen. After a period of one hour the sparging was terminated and 24.15 grams (0.2126 moles) of cysteamine hydrochloride was added to the flask. The mixture was stirred until the cysteamine hydrochloride had completely dissolved. To this stirred mixture was added 120.2 grams of the dried Rohm& Haas Amberlyst A-121 resin. The resin was stirred for 4 hours than the resin was separated from the aqueous solution by filtration. The resulting resin was washed with 16 liters of 18-Mega ohm de-ionized water. The resin was dried overnight in a vacuum oven at 80 C and 27.5" of vacuum. After cooling the resin was removed from the oven yielding 131.8 grams (96.7%) of an attached promoter resin. The resin was stored in a sealed jar.

b. Monomer Preparation Using the Attached Promoter Resin

To a 3 Liter flask equipped with a condenser, mechanical paddle agitator thermocouple probe and a nitrogen inlet was added 145.16 grams (1.00 moles) of 4-acetoxy benzonitrile and 1393 grams (14.80 moles) of phenol. The mixture was heated to 85° C. via a heating mantle controlled by the thermocouple probe and a solid-state controller. When the temperature reached 85° C., 61.0 grams of the attached promoter resin was added to the stirred mixture. The reaction mixture was maintained at 85° C. for a period of 172 hours, with periodic monitoring of the reaction mixture composition by HPLC. The final hot reaction mixture was filtered through a heated flitted disc funnel to separate the ion exchange resin from the liquid phase. The ion exchange resin was washed with 250 grams of hot phenol. The hot phenol rinse was combined with the reaction liquid phase.

The combined liquid phase was subjected to a vacuum distillation with the pot temperature gradually rising from 85° C. to 105° C. The resulting distillate (phenol) was condensed with a tempered water condenser. The pot solidified at the end of the reaction and the resulting solid was re-crystallized from hot methanol/water mixtures five times, yielding a white solid—219.4 grams (69.7%) with HPLC purity of 99% and a melting point of 213.3° C.-213.9° C.

Example 3

A 500 mL Morton flask was charged with 4-(1,1-bis(4-hydroxyphenyl)ethyl)benzonitrile, 3.15 g (10 mmol), BPA, 9.12 g (40 mmol), p-cumylphenol 0.21 g (1 mmol), 125 mL of DI water, 175 mL of dichloromethane and 100 µL of triethylamine. The pH of the rapidly stirred 2 phase system was adjusted to 10.5 with 50 wt % aqueous sodium hydroxide and maintained at 10.5 as phosgene, 9.0 g (90 mmol) was added at 0.5 g/min. The final pH of the reaction mix was 10.7 and 20.0 g of sodium hydroxide solution was required. The polymer solution was separated from the brine by centrifugation and washed 2 times with 100 mL of 1 N HCl followed by 3 times with DI water. The polymer (Sample 3 in Tables 1 and 2, below) was isolated by methanol antisolvent precipitation in a blender. The polymer was filtered, washed with methanol and dried. GPC analysis of the isolated polymer showed $M_w$=79,500 and $M_n$=17,900. DSC (differential scanning calorimetry) showed a glass transition temperature of about 174° C.

Example 4

A 500 mL Morton flask was charged with 4-(1,1-bis(4-hydroxyphenyl)ethyl)benzonitrile, 15.7 g (50 mmol), p-cumylphenol 0.21 g (1 mmol), 125 mL of DI water, 175 mL of dichloromethane and 100 µL of triethylamine. The pH of the rapidly stirred 2 phase system was adjusted to 10.5 with 50 wt % aqueous sodium hydroxide and maintained at 10.5 as phosgene, 9.0 g (90 mmol) was added at 0.5 g/min. The final pH of the reaction mix was 10.7 and 20.8 g of sodium hydroxide solution was required. The polymer solution was separated from the brine by centrifugation and washed 2 times with 100 mL of 1 N HCl followed by 3 times with DI water. The polymer (Sample 8 in Tables 1 and 2, below) was isolated by methanol antisolvent precipitation in a blender. The polymer was filtered, washed with methanol and dried.

GPC analysis of the isolated polymer showed a bimodal distribution $M_w$=48,200 and $M_n$=7,000. DSC (conducted according to ASTM D3418) analysis showed a glass transition temperature (Tg) of about 224° C. Table 1, below, summarizes the properties of the cyano-modified polycarbonate resins prepared according to Examples 3 and (Samples 3 and 8 in Tables 1 and 2, respectively), as well as other samples prepared using similar methodology.

The copolymers prepared in these examples were of formula II, below:

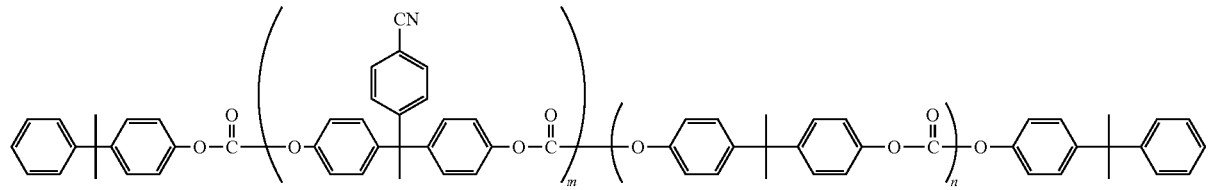

(II)

Wherein the amount of the repeating units m ranges from about 1% to about 100%, and the amount of repeating units n ranges from about 0% to about 99%.

TABLE 1

| SAMPLE # | CYANO-BPA level (mole %) | Carbonate type | Process of preparation | Tg (° C.) | Mw (g/mol) |
|---|---|---|---|---|---|
| Sample 1 (Control, no Cyano-BPA) | 0 | Phosgene | Interfacial | 153 | 46,857 |
| Sample 2 | 8 | Phosgene | Interfacial | 158 | 51,177 |
| Sample 3 | 20 | Phosgene | Interfacial | 174 | 79,500 |
| Sample 4 | 20 | Phosgene | Interfacial | 171 | 55,000 |
| Sample 5 | 35 | Phosgene | Interfacial | 184 | |
| Sample 6 | 50 | Phosgene | Interfacial | 195 | 71,736 |
| Sample 7 | 75 | Phosgene | Interfacial | 208 | 40,425 |
| Sample 8 | 100 | Phosgene | Interfacial | 224 | 48,200 |

As shown, each of the embodiments provided not only a higher Tg than the comparative sample, but also, much higher molecular weights. Also, these examples show that increasing levels of cyano-BPA (or lower ratios of BPA/Cyano-BPA, also referred to herein as Formula III/Formula IV) result in polycarbonate resins having higher glass transition temperatures.

The above resins were solvent cast into films, and the breakdown strength, dielectric constant at 30° C. and 100° C. and tan delta at 30° C. and 100° C. were measured. More specifically, measurements for dielectric breakdown strength were made according to ASTM D149-09, and measurements of dielectric constant and dissipation factor were made according to ASTM D150-98. A summary of the results of these analyses for Examples 3 and 8, as well as for other formulations, are provided below in Table 2:

As shown, the BPA/cyano-BPA (Formula III/Formula IV) molar ratio was adjusted to obtain resins of different properties. The addition of cyano-BPA to polycarbonates made from phosgene and BPA increased the glass transition temperature, Tg, of the resin, and up to a certain level of cyano-BPA also the dielectric constant, Dk, of the resin, without appreciably affecting the dielectric loss or breakdown strength of the material. The addition of Cyano-BPA monomer increased the Tg of polycarbonate from about 150° C. to 224° C., making these compositions suitable for applications requiring relatively high continuous use operating temperatures. The addition of cyano-BPA monomer increased the Dk of polycarbonate up to a certain level (between ~20 and 30 mole %), and then decreased. The maximum values of Dk measured in these formulations were around 4.1-4.3. The dissipation factor of the cyano-containing polycarbonates did not differ appreciably from that of a control containing only BPA.

Figure 5:
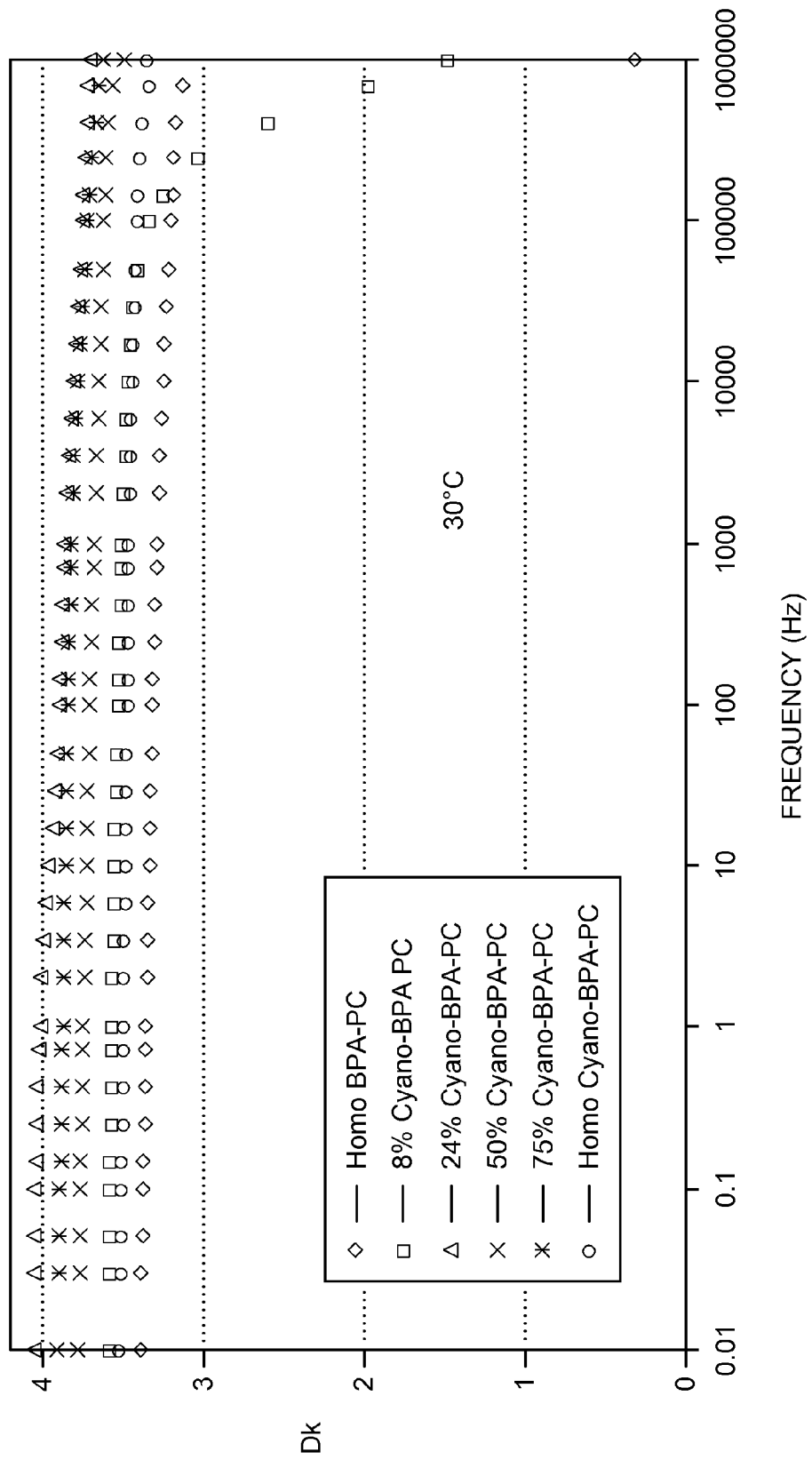
FIG. 5 is a graphical depiction of the dielectric constant as a function of frequency at 30° C. of comparative polycarbonate films and polycarbonate films according to some embodiments.
Figure 7:
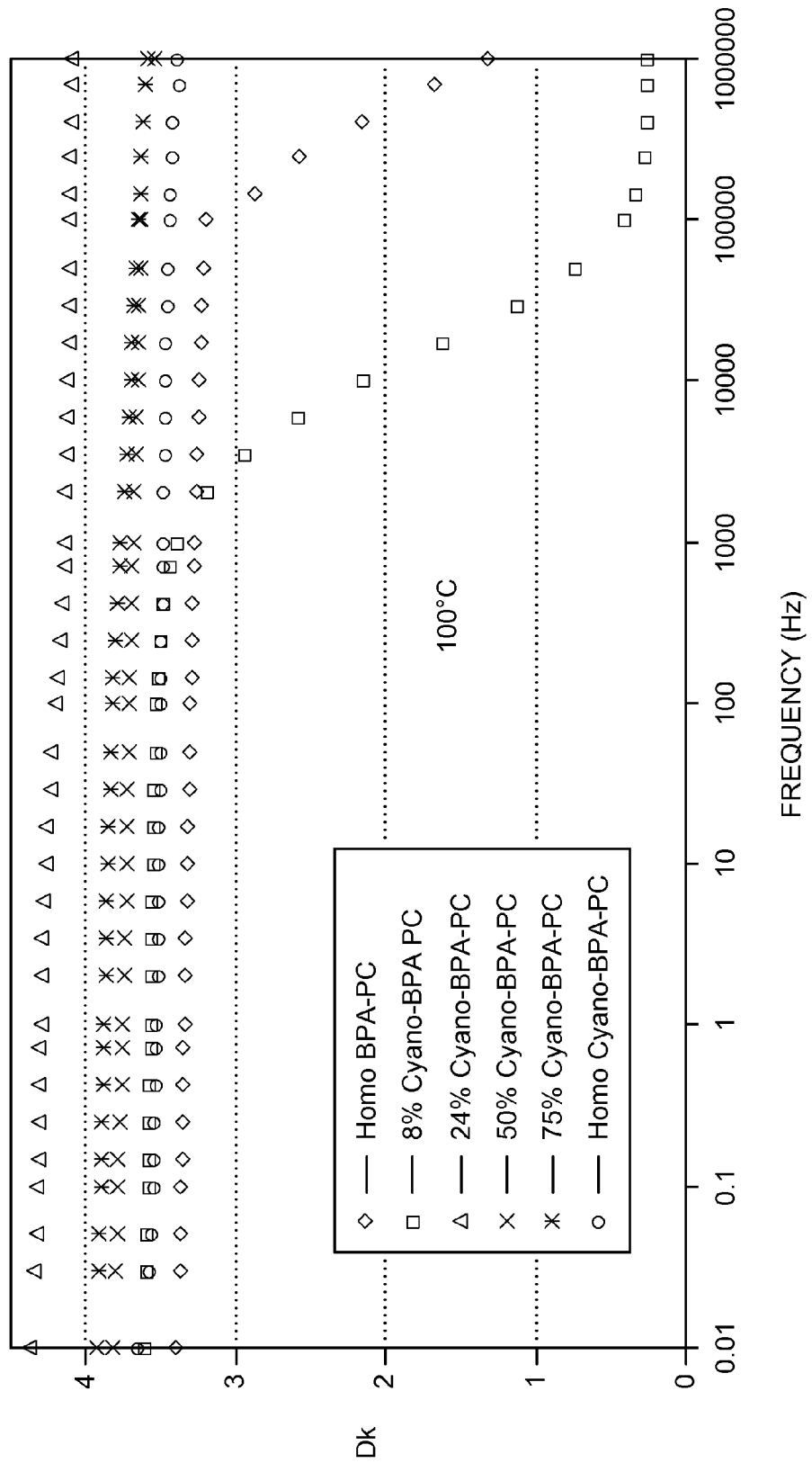
FIG. 7 is a graphical depiction of the dielectric constant as a function of frequency at 100° C. of comparative polycarbonate films and polycarbonate films according to some embodiments.

FIGS. 5 and 7 show the dielectric constant data obtained at different frequencies, and at 30° C. and 100° C., respectively, of polycarbonate compositions containing different levels of the cyano-BPA (Formula IV) monomer. In FIGS. 5 and 7, the Y-axis represents the dielectric constant, which is a dimensionless quantity, and the X-axis represents the applied frequency measured in Hz. As shown in the legends provided with each graph, the individual plots represent the variation of dielectric constant of the polycarbonate film prepared with varying molar ratios of BPA/Cyano-BPA. As can be seen, the dielectric constant varies between about 3 and 4.5, depending on the frequency, temperature and level of cyano-BPA added. These results indicate stability of a capacitor comprising the polycarbonate film as a dielectric over a wide range of applied frequencies at varying temperatures.

Figure 6:
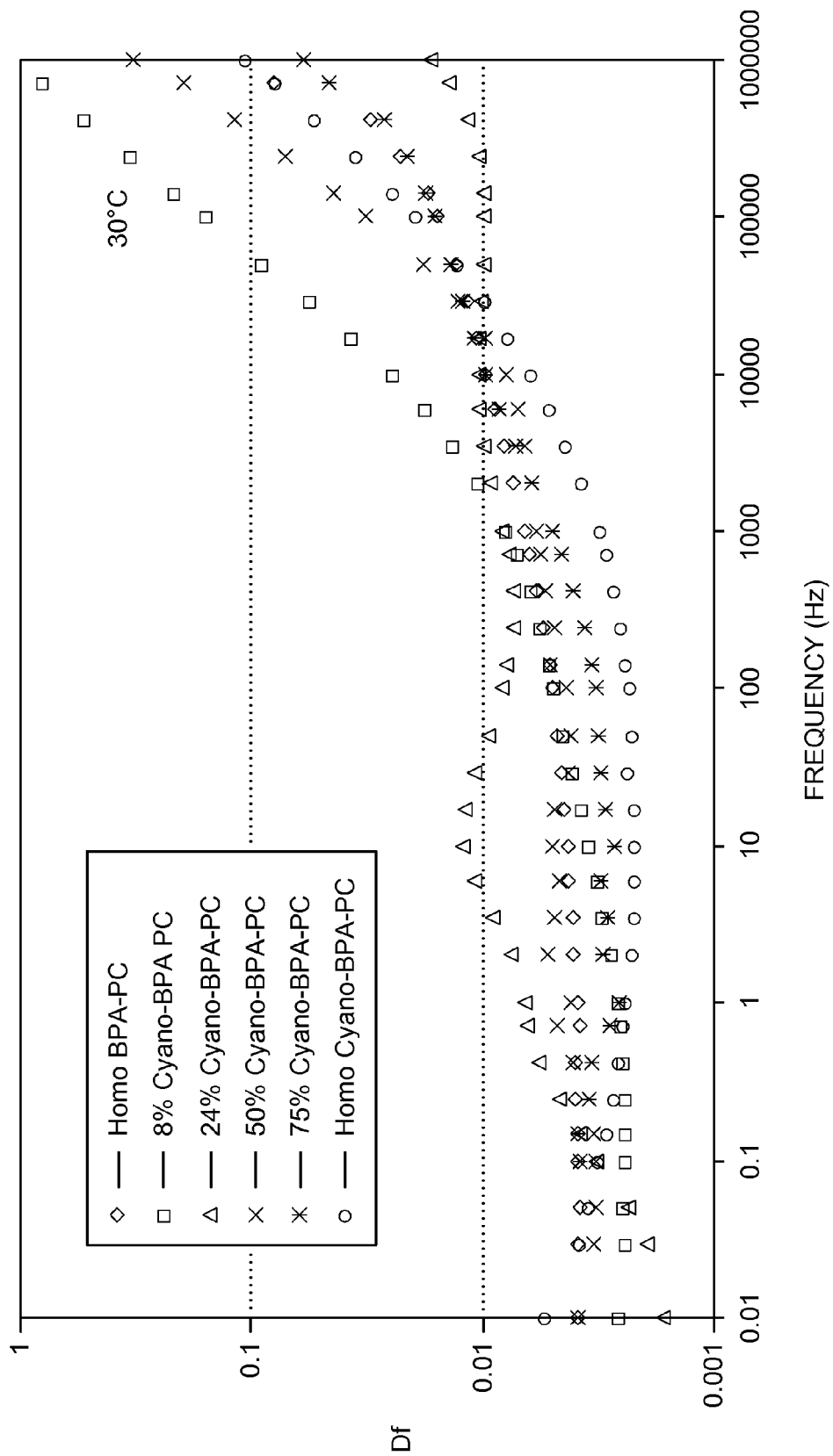
FIG. 6 is a graphical depiction of the dissipation loss (Df) as a function of frequency at 30° C. of comparative polycarbonate films and polycarbonate films according to some embodiments.
Figure 8:
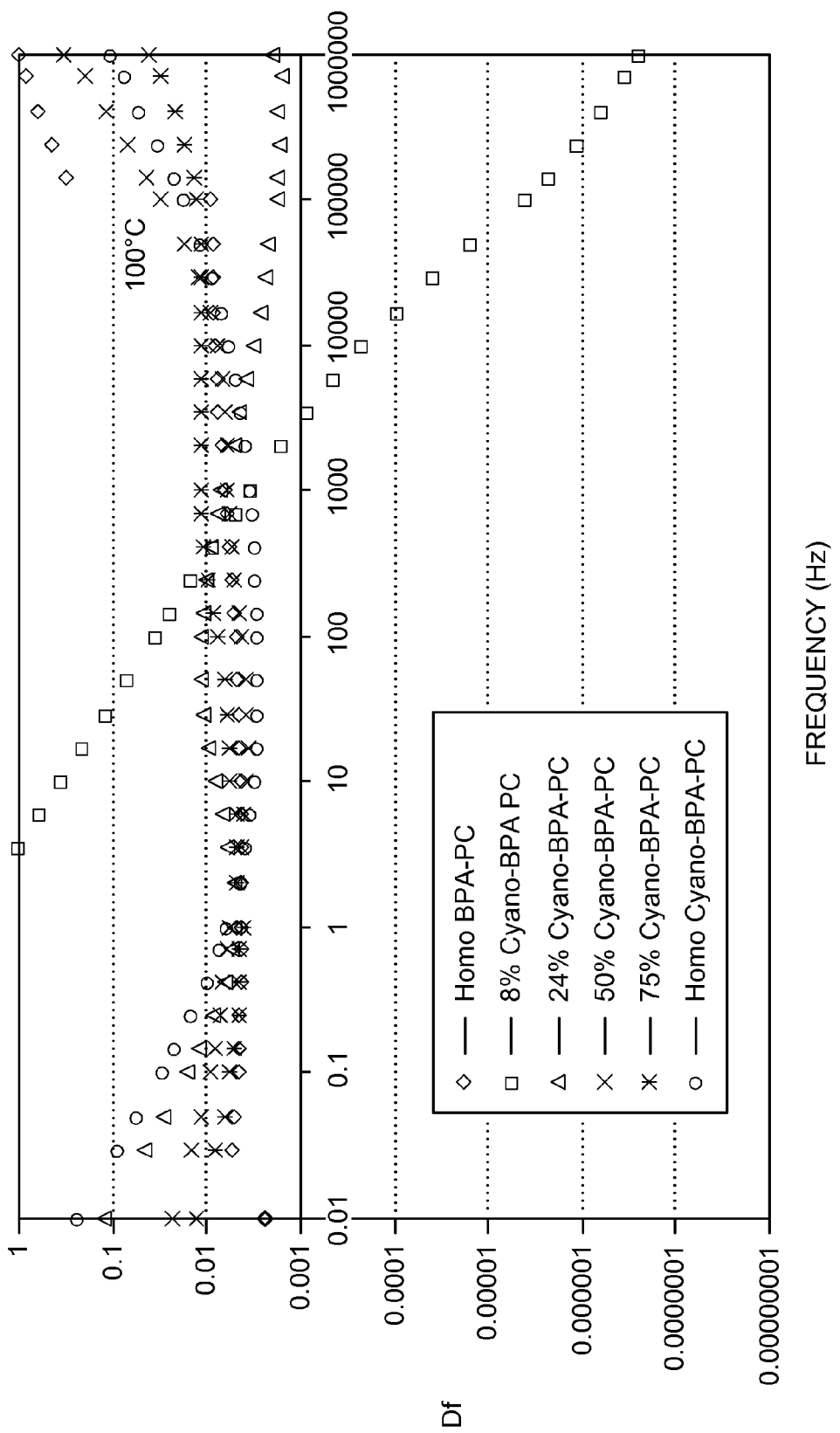
FIG. 8 is a graphical depiction of the dissipation loss (Df) as a function of frequency at 100° C. of comparative polycarbonate films and polycarbonate films according to some embodiments.

FIGS. 6 and 8 are graphical comparisons of the dissipation factor (Df) of polycarbonate films prepared with varying molar ratios of BPA/Cyano-BPA. The data shown in FIG. 6 was obtained at 30° C. and different frequencies, while the

TABLE 2

| SAMPLE # | Breakdown Strength (V/micron) | Film thickness (micron) | Dielectric Constant @30° C. (1000 Hz) | Tan delta @30° C. (1000 Hz) | Dielectric Constant @100° C. (1000 Hz) | Tan delta @100° C. (1000 Hz) |
|---|---|---|---|---|---|---|
| Sample 1 (Control, no Cyano-BPA) | 583 +/− 37 | 34.6 +/− 0.7 | 3.29 | 0.0066 | 3.28 | 0.0063 |
| Sample 2 | 475 +/− 42 | 34.2 +/− 1.8 | 3.5 | 0.0079 | 3.39 | 0.0034 |
| Sample 3 | 363 +/− 83 | 35.0 +/− 1.8 | 3.86 | 0.0083 | 4.14 | 0.0071 |
| Sample 4 | 290 +/− 34 | 15.1 +/− 2.8 | 4.30 | 0.0050 | | |
| Sample 5 | 460 +/− 85 | 15.8 +/− 4.1 | 4.14 | 0.0059 | 4.12 | 0.0073 |
| Sample 6 | 543 +/− 69 | 15.5 +/− 1.3 | 3.68 | 0.0058 | 3.68 | 0.0059 |
| Sample 7 | 545 +/− 60 | 14.6 +/− 1.3 | 3.77 | 0.0040 | 3.76 | 0.0114 |
| Sample 8 | 344 +/− 66 | 31.5 +/− 4.2 | 3.46 | 0.0031 | 3.48 | 0.0033 |

Solvent Cast Films data shown in FIG. 8 was obtained at 100° C. and different frequencies. In both FIGS, the Y-axis represents the dissipation factor, which is a dimensionless quantity, and the X-axis represents the applied frequency in Hz. These results show that the polycarbonate resins of this invention had dissipation factors that were below about 1% for the frequencies of interest.

Figure 9:
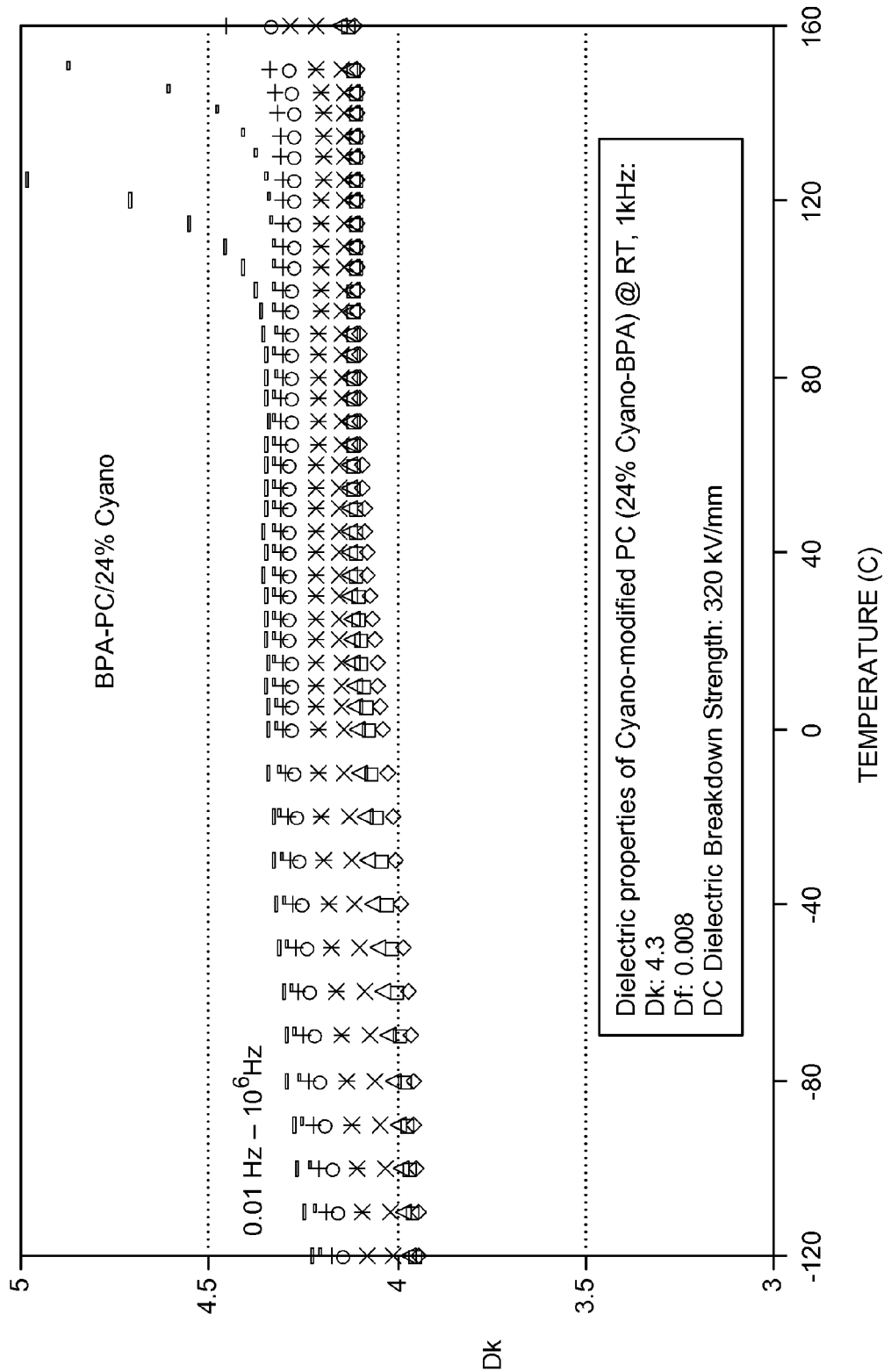
FIG. 9 is a graphical depiction of the dielectric constant as a function of temperature and frequency of a polycarbonate film according to one embodiment.

FIG. 9 is a graphical depiction of the dielectric constant as a function of temperature and frequency of a polycarbonate film made from a polymer containing 24 mole % of the cyano-BPA monomer. These results show that the polymer film had a dielectric constant of 4.3 and dissipation factor of 0.008 when tested at room temperature and 1 kHz. The DC dielectric breakdown strength of such a film tested in a separate experiment was 320 kV/mm.

The present invention has been described in terms of some specific embodiments. They are intended for illustration only, and should not be construed as being limiting in any way. Thus, it should be understood that modifications can be made thereto, which are within the scope of the invention and the appended claims. Furthermore, all of the patents, patent applications, articles, and texts which are mentioned above are incorporated herein by reference.

The invention claimed is:

1. A polycarbonate resin, having a repeating unit of formula I:

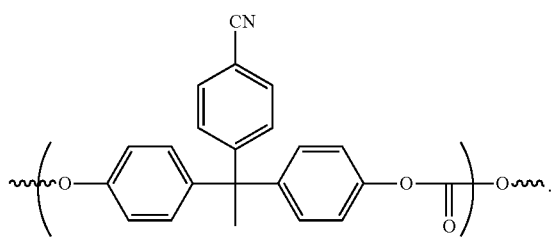

(I)

2. The polycarbonate resin of claim 1, of formula II

3. The polycarbonate resin of claim 1, wherein the amount of the repeating units m of formula II ranges from about 1% to about 100%.

4. The polycarbonate resin of claim 1, wherein the amount of the repeating units n of formula II ranges from about 0% to about 99%.

5. A thin film comprising the polycarbonate resin of claim 1.

6. An electronic article, comprising the thin film of claim 5.

7. The electronic article of claim 6, comprising a capacitor, sensor, battery, flexible printed circuit board, keyboard membrane, motor/transformer insulation, cable wrapping, industrial tape, or interior coverage material.

8. A capacitor comprising:

A thin film comprising a polycarbonate resin having a repeating unit of the formula I:

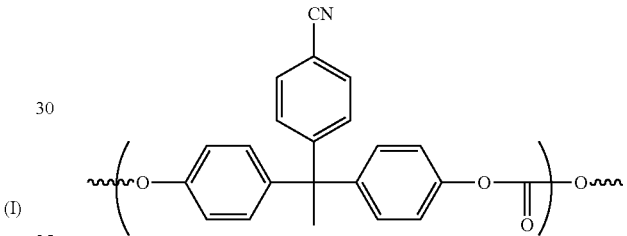

(I)

a metallized layer disposed on a first surface of the polycarbonate film; and an electrode disposed on a second surface of the polycarbonate film.

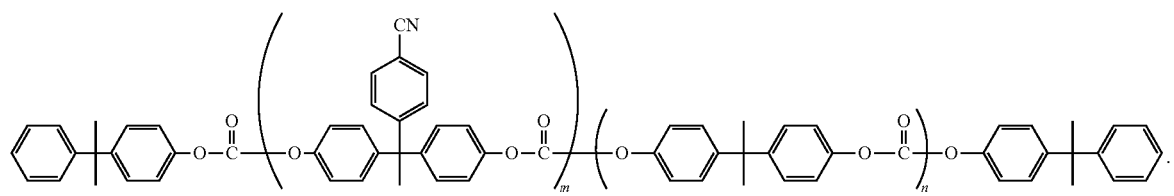

(II)

9. The capacitor of claim 8, wherein the polycarbonate resin has a Formula II

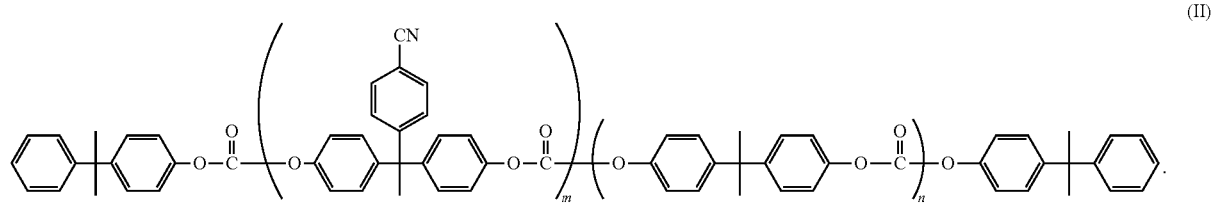

10. The capacitor of claim 9, wherein the amount of the repeating units m of formula II ranges from about 1% to about 100%.

11. The capacitor of claim 9, wherein the amount of the repeating units n of formula II ranges from about 0% to about 99%.

12. The capacitor of claim 9, wherein a dielectric layer comprising the polycarbonate resin has a breakdown strength of at least about 275 V/micron and a dielectric constant of at least about 3.3.

13. The capacitor of claim 9, wherein the polycarbonate resin further comprises at least one filler.

14. The capacitor of claim 13, wherein the filler has a largest dimension of from about 0.1 nm to about 1000 nm and is present in the polycarbonate resin in an amount of less than about 20 weight percent, based upon the total weight of the polycarbonate resin.

15. A monomer of formula III

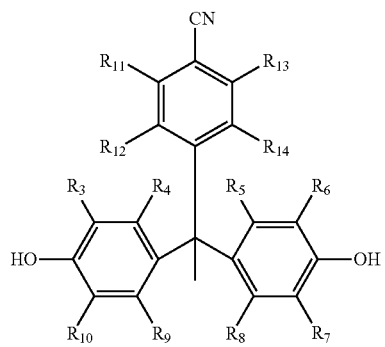

Wherein $R_3$-$R_{10}$ are independently a hydrogen atom, halogen atom, nitro group, cyano group, $C_1$-$C_{20}$ alkyl radical $C_4$-$C_{20}$ cycloalkyl radical, or $C_4$-$C_{20}$ aryl radical; $R_{11}$-$R_{14}$ are each independently a hydrogen atom, $C_1$-$C_{20}$ alkyl radical, $C_4$-$C_{20}$ cycloalkyl radical, or $C_4$-$C_{20}$ aryl radical; or $R_{11}$ and $R_{12}$ together form a $C_4$-$C_{20}$ cycloaliphatic ring which is optionally substituted by one or more $C_1$-$C_{20}$ alkyl, $C_6$-$C_{20}$ aryl, $C_5$-$C_{20}$, aralkyl, $C_5$-$C_{20}$ cycloalkyl groups or a combination thereof.

16. A method for preparing the monomer of claim 15, comprising reacting phenol with 4-acetoxy benzonitrile in the presence of an acid catalyst.

17. The method of claim 16, wherein the acid catalyst comprises a soluble mineral acid, a soluble organic acid or combinations of these.

18. The method of claim 17, wherein the acid catalyst is a soluble mineral acid and comprises sulfuric acid or hydrochloric acid.

19. The method of claim 17, wherein the acid catalyst is a soluble organic acid and comprises methane-sulfonic acid.

\* \* \* \* \*